US006332013B1

(12) United States Patent
Hsieh

(10) Patent No.: US 6,332,013 B1
(45) Date of Patent: Dec. 18, 2001

(54) METHODS AND APPARATUS FOR TILTED HELICAL RECONSTRUCTION MULTISLICE CT

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/473,341

(22) Filed: Dec. 28, 1999

(51) Int. Cl.$^7$ ........................................ A61B 6/03
(52) U.S. Cl. ................... 378/15; 378/4; 378/901
(58) Field of Search ............ 378/4, 8, 15, 19, 378/901

(56) References Cited

U.S. PATENT DOCUMENTS

| | | | |
|---|---|---|---|
| 5,815,546 | * | 9/1998 | Flohr et al. ............... 378/19 |
| 6,061,420 | * | 5/2000 | Strong et al. ............. 378/4 |
| 6,118,841 | * | 9/2000 | Lai .......................... 378/19 |
| 6,229,869 | * | 5/2001 | Hu ........................... 378/4 |

FOREIGN PATENT DOCUMENTS

WO-9918854-A1 * 4/1999 (WO).

* cited by examiner

Primary Examiner—David V. Bruce
(74) Attorney, Agent, or Firm—Armstrong Teasdale LLP; Christian G. Cabou

(57) ABSTRACT

In one aspect, the present invention is a method for filtering projection data of a computed tomographic scan of an object. The method includes steps of: acquiring projection data representing a tilted, helical scan of an object; zero padding the acquired projection data; determining a Fourier transform of the zero padded projection data; determining a product of the Fourier transform of the zero padded projection data, a ramp function, and a phase shift function; and determining an inverse Fourier transform of the multiplied, transformed projection data as filtered projection data.

The above-described method provides filtered data that produces compensated tilted, helically scanned CT images having significantly better spatial resolution than those methods employing a high frequency kernel boost.

18 Claims, 3 Drawing Sheets

METHODS AND APPARATUS FOR TILTED HELICAL RECONSTRUCTION MULTISLICE CT

BACKGROUND OF THE INVENTION

This invention relates generally to methods and apparatus for computed tomography (CT) imaging of objects, and more particularly to methods and apparatus for producing compensated tilted, helically scanned CT images of objects.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In known multislice CT imaging systems, gantry tilt is disabled for helical scans. When the gantry is tilted, degraded image quality results because the isocenter is inherently detector row dependent. The isocenter is shifted relative to the patient scanning axis, and the amount of shift depends upon detector row, amount of gantry tilt, and projection angle.

For example, and referring to FIG. 3, an axial scan of a human skull is depicted for a 1.25 mm slice thickness. The gantry was tilted at −20° and no projection weighting was applied in the reconstruction of the image of FIG. 3. This image was reconstructed with a 15 cm field of view (FOV) and a high-resolution algorithm to illustrate fine structural details of the scanned phantom. This image serves as a standard for image quality evaluation, as no degradation is present in a tilted axial scan mode.

For comparison, the same phantom used to generate the image of FIG. 3 was scanned in a helical mode with 1.25 mm slice thickness at 3:1 helical pitch to generate the image shown in FIG. 4. For generating this image, a helical scan was performed in which the patient table was moved 3.75 mm per gantry rotation. The image of FIG. 4 was reconstructed without z-smoothing, and the same reconstruction parameters were used as those of FIG. 3. The fine bony structures are blurred in FIG. 4 as a result of the isocenter shift.

It might be expected that isocenter shift could be corrected by a compensation algorithm that interpolates projection data to a desired location. Such algorithms turn out to be somewhat effective in combating double blurring structures. However, spatial resolution of reconstructed images is compromised because the interpolation kernel acts as a low pass filter to the projection data. To partially compensate for resolution degradation, a high frequency kernel boost can be introduced to "sharpen" the image. However, spatial resolution cannot be recovered. An example of a "sharpened" image is shown in FIG. 5, which depicts a "sharpened" version of the same scan as shown in FIG. 4. Compared to the axially-scanned image of FIG. 3, the loss of spatial resolution is obvious. (The rotation of FIG. 5 is due to implementation artifacts, and is unrelated to the reconstruction and "sharpening" algorithms.)

It would therefore be desirable to provide methods and apparatus for filtering data to produce compensated tilted, helically scanned CT images of objects.

BRIEF SUMMARY OF THE INVENTION

There is therefore provided, in one embodiment, a method for filtering projection data of a computed tomographic scan of an object. The method includes steps of: acquiring projection data representing a tilted, helical scan of an object; zero padding the acquired projection data; determining a Fourier transform of the zero padded projection data; determining a product of the Fourier transform of the zero padded projection data, a ramp function, and a phase shift function; and determining an inverse Fourier transform of the multiplied, transformed projection data as filtered projection data.

The above-described method provides filtered data that produces compensated tilted, helically scanned CT images having significantly better spatial resolution than those methods employing a high frequency kernel boost.

BRIEF DESCRIPTION OF THE DRAWINGS

FIG. 3 is an axial scan of the phantom without application of projection weighting. FIG. 4 is a helical scan at 3:1 helical pitch, reconstructed without z-smoothing. FIG. 5 is a "sharpened" version of the same scan shown in FIG. 4, using a high-frequency kernel boost FIG. 6 is a version of the same scan shown in FIG. 4, but using data to which a method embodiment of the present invention has been applied.

DETAILED DESCRIPTION OF THE INVENTION

Figure 1:
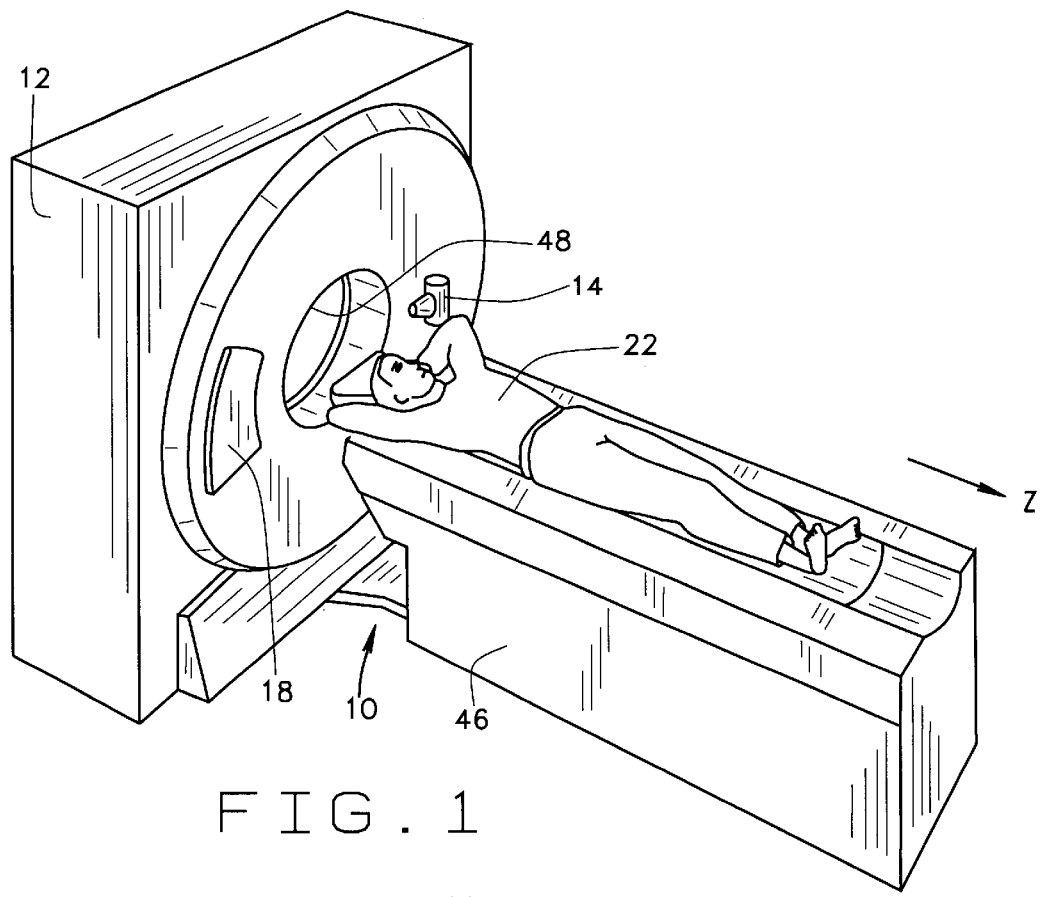
FIG. 1 is a pictorial view of a CT imaging system.
Figure 2:
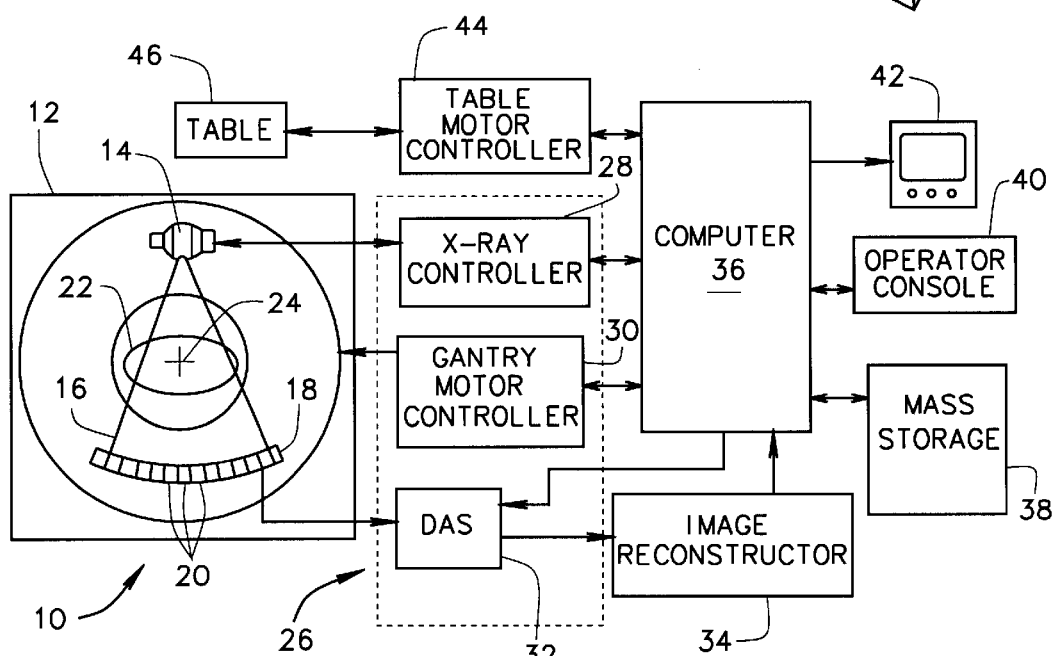
FIG. 2 is a block schematic diagram of the system illustrated in FIG. 1.
Figure 3:
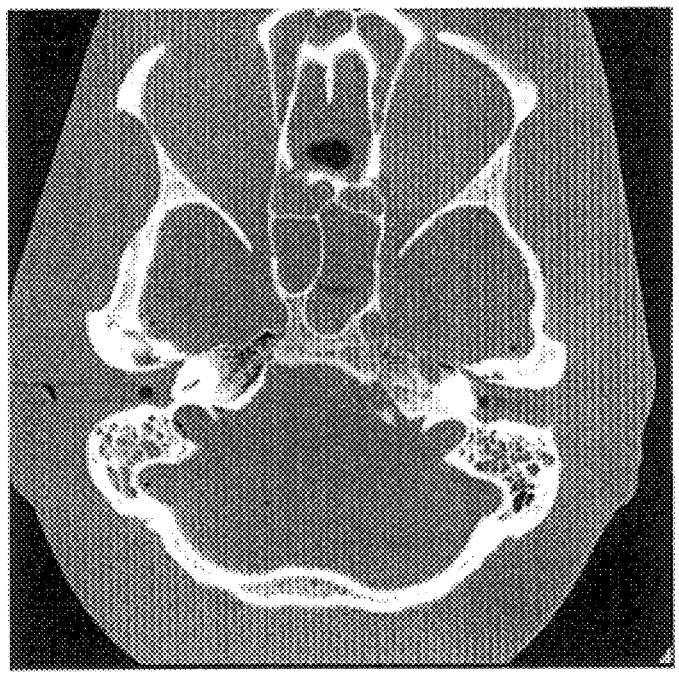
FIGS. 3–6 are reconstructed images of the same phantom, each scanned with −20 gantry tilt, reconstructed using a high-resolution algorithm, and having DFOV=15 mm.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment of the present invention employing a filtered back projection reconstruction, the Fourier transform of a measured projection is readily available. Therefore, a first step of the filter process is to perform a Fourier transform of a zero padded projection. The transformed projection is then multiplied by a ramp function and a phase-shift function, zero padded, and inversely Fourier transformed to arrive at the filtered projection.

In the following explanation of an embodiment employing Fourier transforms, $p(\gamma, \beta, n)$ denotes the measured projection data with detector angle $\gamma$, view angle $\beta$, and detector row number n. In addition, for ease of discussion, it is assumed that a measured projection is shifted relative to a patient-based isocenter by $\Delta\gamma$, where $\Delta\gamma$ depends upon $\beta$, n, gantry tilt angle, x-ray beam width, and source to isocenter distance. An ideal projection, $u(\gamma, \beta, n)$ relates to a measured projection by a relationship written as:

$$u(\gamma, \beta, n) = p(\gamma - \Delta\gamma, \beta, n)$$

By performing a Fourier transform on both sides of the equation above with respect to $\gamma$, the following equation is written:

$$U(\omega, \beta, n) = F\{u(\gamma, \beta, n)\} = F\{p(\gamma - \Delta\gamma, \beta, n)\} = e^{-j\omega\Delta\gamma} P(\omega, \beta, n)$$

The above equation is a consequence of the Fourier shift theorem, which states that a shift in the spatial domain is equivalent to a phase shift in the frequency domain.

In one embodiment of the present invention, projection data are weighted and summed before the filtering operation for computational performance. Denoting by k the number of rows that are summed for a particular projection angle, k Fourier transforms of the original projection and one inverse Fourier transform are required.

Figure 4:
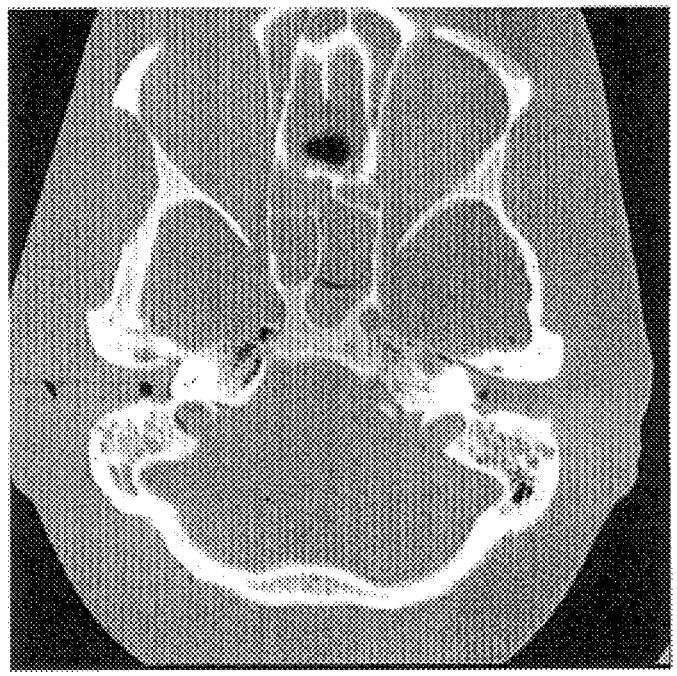
Figure 5:
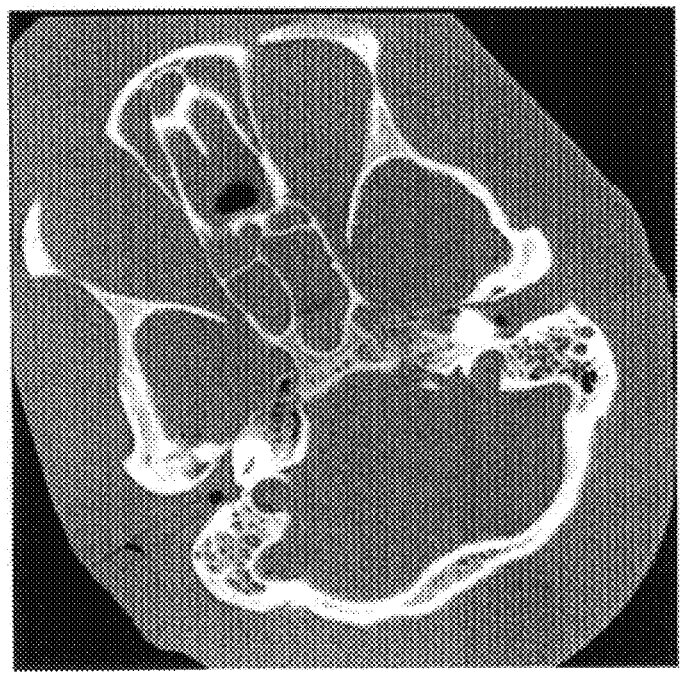
Figure 6:
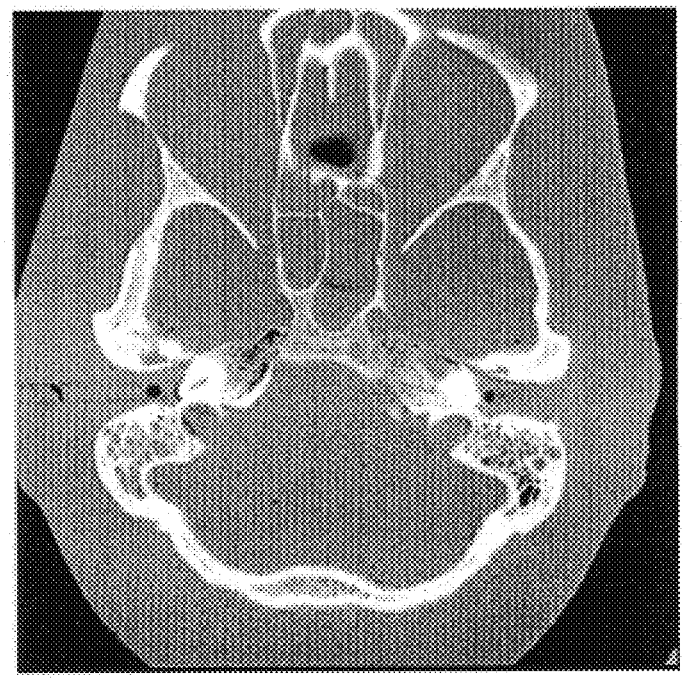

The helical scan of FIG. 4 is shown reconstructed in FIG. 6 using an embodiment of the present invention. A Fourier transformed projection is multiplied by a ramp projection and a phase shift function, zero padded, and inversely Fourier transformed to arrive at the filtered projection. A significant improvement in spatial resolution is evident compared to FIG. 5. The reconstructed object is nearly as sharp as the axial scan illustrated in FIG. 4. Some slight degradation in some fine structures may result from the constant translation of the patient table in the helical scan mode. Some streaking is also evident because aliasing is increased. The increased aliasing results from destruction of quarter detector offset sampling by the detector row-dependent isocenter shift. Because the image of FIG. 6 was reconstructed with a high-resolution algorithm, double sampling from quarter detector offset is needed for aliasing cancellation. In one embodiment, increased aliasing is overcome by deliberately misaligning the isocenter in back-projection. In another embodiment, a bias is added in the phase shift to achieve the same purposes. For example, if a projection was shifted by $\delta$ with respect to an "ideal" location, the "misaligned" projection is shifted by $-c \cdot \delta$, where c is a parameter $0 > c \leq 1$.

In one embodiment of the present invention, the methods described above are carried out in CT imaging system 10 in which, for example, a tilt angle of gantry 12 is selectable relative to table 46. DAS 32 converts signals received from a multislice detector 18 into data for subsequent processing by computer 36. In one embodiment, computer 36 also establishes a tilt angle for gantry 12. Data processing steps for filtering the acquired projections are also performed by computer 36.

In the previous description, the phase shift operation is performed right after the ramp filter operation. However, because complex multiplication is linear, in another embodiment, a combined filter (ramp multipled by the phase shift) is pre-calculated, stored, and multiplied by the Fourier transform for computational efficiency.

From the preceding description of various embodiments of the present invention, it is evident that the methods and apparatus described herein provide filtered projection data from tilted helical scans of an object. The filtered projection data can then be reconstructed to provide improved, high-spatial resolution images of the object.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for filtering projection data of a computed tomographic scan of an object; said method comprising the steps of:

acquiring projection data representing a tilted, helical scan of an object;

zero padding the acquired projection data;

determining a Fourier transform of the zero padded projection data;

determining a product of the Fourier transform of the zero padded projection data, a ramp function and a phase shift function; and determining an inverse Fourier transform of the product of the Fourier transform, the ramp function, and the phase shift function as filtered projection data.

2. A method in accordance with claim 1 wherein determining a product of the Fourier transform of the zero-padded projection data, a ramp function and a phase shift function comprises the steps of pre-calculating a product of the ramp function and the phase shift function, and multiplying the Fourier transform of the zero-padded projection data by the pre-calculated product.

3. A method in accordance with claim 1 and further comprising the step of weighting and summing the phase-shifted Fourier transform of the zero padded projection data.

4. A method in accordance with claim 1 and further comprising the step of adding a bias to the phase shift to provide aliasing compensation.

5. A method in accordance with claim 1 and further comprising the step of selectively misaligning an isocenter in backprojection to provide aliasing compensation.

6. A method in accordance with claim 1 wherein $p(\gamma, \beta, n)$ denotes measured projection data with detector angle $\gamma$, view angle $\beta$, and detector row number n, a measured projection is shifted relative to an object based isocenter by $\Delta\gamma$, where $\Delta\gamma$ depends upon $\beta$, n, gantry tilt angle, radiation beam width, and source to isocenter distance, an ideal projection $u(\gamma, \beta, n)$ relates to a measured projection by a relationship written as:

$$u(\gamma, \beta, n) = p(\gamma - \Delta\gamma, \beta, n),$$

and further comprising the step of determining an estimated Fourier transform of ideal projection $U(\omega, \beta, n)$ from a Fourier transform of measured projection $P(\omega, \beta, n)$ using a relationship written as:

$$U(\omega, \beta, n) = e^{-j\omega\Delta\gamma} P(\omega, \beta n).$$

7. A method in accordance with claim 6 and further comprising the step of weighting and summing the phase-shifted Fourier transform of the zero padded projection data.

8. A method in accordance with claim 6 and further comprising the step of adding a bias to the phase shift to provide aliasing compensation.

9. A method in accordance with claim 6 and further comprising the step of selectively misaligning an isocenter in backprojection to provide aliasing compensation.

10. A computed tomographic (CT) imaging system configured to:

acquire projection data representing a tilted, helical scan of an object;

zero pad the acquired projection data;

determine a Fourier transform of the zero padded projection data;

determine a product of the Fourier transform of the zero padded projection data, a ramp function and a phase shift function; and determine an inverse Fourier transform of the product of the Fourier transform, the ramp function, and the phase shift function as filtered projection data.

11. A CT imaging system in accordance with claim 10 wherein said system being configured to determine a product of the Fourier transform of the zero-padded projection data, a ramp function and a phase shift function comprises said system being configured to pre-calculate a product of the ramp function and the phase shift function, and to multiply the Fourier transform of the zero-padded projection data by the pre-calculated product.

12. A CT imaging system in accordance with claim 10 further configured to weight and sum the phase-shifted Fourier transform of the zero padded projection data.

13. A CT imaging system in accordance with claim 10 further configured to add a bias to the phase shift to provide aliasing compensation.

14. A CT imaging system in accordance with claim 10 further configured to selectively misaligned an isocenter in backprojection to provide aliasing compensation.

15. A CT imaging system in accordance with claim 10 wherein $p(\gamma, \beta, n)$ denotes measured projection data with detector angle $\gamma$, view angle $\beta$, and detector row number n, a measured projection is shifted relative to an object based isocenter by $\Delta\gamma$, where $\Delta\gamma$ depends upon $\beta$, n, gantry tilt angle, radiation beam width, and source to isocenter distance, an ideal projection $u(\gamma, \beta, n)$ relates to a measured projection by a relationship written as:

$$u(\gamma, \beta, n) = p(\gamma - \Delta\gamma, \beta, n),$$

and an estimated Fourier transform of ideal projection $U(\omega, \beta, n)$ is, determined from a Fourier transform of measured projection $P(\omega, \beta, n)$ using a relationship written as:

$$U(\omega, \beta, n) = e^{-j\omega\Delta\gamma} P(\omega, \beta, n).$$

16. A CT imaging system in accordance with claim 15 further configured to weight and sum the phase-shifted Fourier transform of the zero padded projection data.

17. A CT imaging system in accordance with claim 15 further configured to add a bias to the phase shift to provide aliasing compensation.

18. A CT imaging system in accordance with claim 15 further configured to selectively misaligned an isocenter in backprojection to provide aliasing compensation.

* * * * *

UNITED STATES PATENT AND TRADEMARK OFFICE
CERTIFICATE OF CORRECTION

PATENT NO. : 6,332,013 B1  Page 1 of 1
DATED : December 18, 2001
INVENTOR(S) : Jiang Hsieh It is certified that error appears in the above-identified patent and that said Letters Patent is hereby corrected as shown below:

Column 5,
Line 35, delete "$P(\omega, \beta n).$" and insert therefor -- $P(\omega, \beta, n).$ --.

Column 6,
Lines 22 and 50, delete "misaligned" and insert therefor -- misalign --.

Signed and Sealed this

Fourth Day of November, 2003

JAMES E. ROGAN
*Director of the United States Patent and Trademark Office*